United States Patent [19]
Salort

[11] Patent Number: 4,593,697
[45] Date of Patent: Jun. 10, 1986

[54] EXTERNAL APPLIANCE FOR THE TRUNK OF THE BODY

[76] Inventor: Guy J. Salort, 219, rue Raymond Losserand, 75014 Paris, France

[21] Appl. No.: 701,177

[22] Filed: Feb. 13, 1985

[30] Foreign Application Priority Data

Feb. 14, 1984 [FR] France ............................ 84 02202

[51] Int. Cl.[4] ............................................. A41C 1/00
[52] U.S. Cl. ................................................. 128/538
[58] Field of Search ............... 128/538, 518, 520, 537, 128/523, 531, 558

[56] References Cited

U.S. PATENT DOCUMENTS

| | | | |
|---|---|---|---|
| 2,139,305 | 12/1938 | Friend | 128/538 |
| 2,530,132 | 11/1950 | Silvain | 128/558 |

Primary Examiner—Doris L. Troutman
Attorney, Agent, or Firm—Brisebois & Kruger

[57] ABSTRACT

An external appliance to be worn on the trunk of a person compensates for lack of tone, metricity and for sensitivity in the vertebral column and trunk. The appliance comprises upper and lower composite structures respectively surrounding the hemithoracic regions and the pelvis and abdomen. The appliance takes into account differential variations in trunk diameter and provides a preferential link between the scapular muscles and pelvic motor muscles of the user.

22 Claims, 8 Drawing Figures

EXTERNAL APPLIANCE FOR THE TRUNK OF THE BODY

INTRODUCTION

The present invention relates to an external appliance for the trunk of the body.

BACKGROUND TO THE INVENTION

Three types of appliance are at present used for people having motor handicaps of the trunk. A first type essentially comprises a rigid or semi-rigid structure encircling the trunk, such as a plastics shell or a corset of metal, leather or a composite of fabric and steel. A second type comprises a rear and/or lateral support cooperating with a corset in order to support the user, and is generally known as a "Lyon corset", whilst the third type comprises elastic corsets encircling the trunk in a homogeneous manner.

These known devices only incompletely satisfy, or do not satisfy at all, the function of reactivating the motor units of the user's trunk, and do not therefore enable the recovery of the motricity or the recovery of sensitivity in the trunk if this has been lost.

SUMMARY OF THE INVENTION

The present invention is designed to provide a device which remedies the above drawbacks to a significant extent.

More precisely the aim of the invention is to provide an appliance or orthosis enabling any disorders involving a lack of tone and/or motricity and/or sensitivity in the vertebral column and/or the trunk of the patient to be more or less completely compensated.

The principle on which the invention is based, consists in the provision of an appliance which is able to take into account differential variations in trunk diameters resulting from respiratory movements or any other voluntary movements of the trunk or parts thereof, and which is able to restore these movements and transmit them in a dynamic manner to the interior of the system, which conserves energy in practice, constituted by the appliance, by providing dynamic support for the muscles involved in respiration, standing and motricity.

In accordance with the invention this is achieved by an independent appliance constituted by a composite, light and movable appliance, which provides a preferential link between the scapular motor muscles and the pelvic motor muscles of the user wearing the appliance. In this way, the appliance of the invention may be advantageously combined with an external appliance for people having motor handicaps involving at least one upper limb and/or an external appliance for people having motor handicaps of at least one lower limb, which are disclosed in French Patent Application No. 82 18 902 and Published European specification No. 0 066 028 respectively. By associating the appliance of the invention with the external paraskeletons of the upper and lower limbs described in the above-mentioned patent applications, it is possible to form an appliance involving the whole of the locomotor apparatus of the patient wearing the appliance. It should also be noted that the appliance of the invention enables the application, with respect to the trunk, of the bio-mechanical principles used as the basis for the development of the front and bearing regions described respectively in the two patent applications described above.

For this purpose the external appliance for the trunk of the body of the present invention, is characterised in that it comprises two composite structures, the first structure being a lower structure, having a general frusto-conical shape, designed to encircle the pelvis and the abdomen and constituted by a pelvic corset extending substantially from the bi-trochanterian perimeter at the base substantially, on one hand, up to the navel at the top and at the front and, on the other hand, the lower half of the lumbar column, at the top and at the back, the corset comprising:
  (a) a plurality of semi-rigid elements connected by flexible and pliable members,
  (b) regulatory elastic means, connecting each of the two portions of the corset located perpendicular to the two anterior superior iliac spines to the portion of the corset located perpendicular to the homolateral sacroiliac joint on one hand, and to the portion of the corset located perpendicular to the homolateral ischium, on the other hand, the second composite structure being an upper structure comprising two symmetrical hemithoracic envelopes, each having a general external frustoconical shape and each surrounding a hemithorax, the two hemithoracic envelopes each having a sterno-xyphoidian portion in common and each comprising two sub-assemblies, one of which is a scapular sub-assembly and the other an inferior lateral thoracic assembly, each of these two sub-assemblies being constituted by a plurality of semi-rigid elements connected by flexible and pliable members, the regions of the axillary space and the breast remaining free, the upper structure also comprising:
  (a) an elastic dorsal articulation, centered at the top of the dorsal column and connecting the two hemithoracic envelopes together in a detachable manner,
  (b) regulatory elastic means connecting, on each of the two hemithoracic envelopes, on one hand, the semi-rigid elements of the scapular sub-assembly, and, on the other hand, the semi-rigid elements of the thoracic sub-assenbly, the two composite structures being connected to one another by connection means and means for regulating the dynamic equilibrium of the appliance, which comprise: --
  (a) two anterior lever springs, each disposed between one of the two portions of the corset located perpendicular to the anterior superior iliac spines and the homolateral portion of the sterno-xyphoidian common portion, the lever springs being designed to take account of the deformations of the trunk due to flexion or torsion and the regulate the relative movements of the vertebral column, the pelvis and the thoracic assembly,
  (b) two lateral posterior tighteners each connecting the sub-spinal zone of the scapular sub-assembly of one of the two hemithoracic envelopes to the portion of the corset located perpendicular to the iliac spine on the opposite side, the said tighteners being designed to prevent the thorax from falling forwards.

In a preferred embodiment, the corset comprises four semi-rigid elements, the two first elements being substantially identical and having the approximate shape of an equilateral triangle one of whose sides is substantially identical to the demi-perimeter of the waist, one of the elements being a rear element which is disposed on the sacro-coccygeal region such that its lower side is disposed along the posterior bi-trochanterian demi-perimeter and the other of the first elements being an anterior element which is disposed on the public symphysis such that its upper side is disposed along the anterior demi-perimeter of the waist, the two other semi-rigid elements of the corset being substantially identical elements substantially of trapezoidal shape each located in an intermediate position between the first anterior and posterior elements, the upper edges of these trapezoidal elements being disposed at the waist and being substantially equal to the demi-perimeter of the waist, these two intermediate elements being disposed symmetrically on each side on the two iliac bones.

In a preferred embodiment, each of the two sub-assemblies of the second composite structure is constituted by three semi-rigid elements connected by flexible and pliant members, the said three semi-rigid elements being, in the case of the scapular sub-assembly, a pectoral element, a trapezoidal element and the sub-spinal element, and, in the case of the thoracic sub-assembly, a posterior thoracic element located on the sub-scapular region, an anterior thoracic element located on the sub-mammary element, and a xyphoidian element located on the costal cartilages and belonging to the common sterno-xyphoidian portion, the two hemithoracic envelopes being connected together by the dorsal elastic articulation at the location of the sub-spinal elements of their scapular sub-assemblies.

Thus, the lower end of the trunk, i.e. the pelvic area, which forms the dynamic foundation of the vertebral column, and the upper ends of the trunk, i.e. the two scapular muscles supported by the dorso-lumbar column, are each encircled by a frustoconical, composite envelope, whose play and differential deformations are regulated by the load of the anterior lever springs, the lateral posterior tighteners and the regulatory elastic means for the corset and the hemithoracic envelopes.

The appliance of the invention therefore enables all physiological movements of the vertebral column. In the case of a medium setting of the lever springs, the tighteners and the regulatory elastic means, the overall anterior flexion of the dorso-lumbar vertebral column may reach 30°, and its lateral inclination may reach 15°, whilst a lateral and superior costal extension may be obtained, as well as all the possible combinations of swivel deformation movements (torsion-extension).

In order to facilitate the positioning and the fastening of the corset on the user, the corset opens and closes advantageously at the front and, for this purpose, the anterior semi-rigid element of the corset is sub-divided, along a vertical and median line, into two halves supporting the additional means of a mechanism for opening and closing the two halves with respect to one another.

In order to facilitate the movements of pelvic muscle in the case of lordosis or kyphosis, the two apices adjacent to the said horizontal side of the anterior and posterior triangular elements of the corset are cut, defining free spaces enabling movements of the pelvis.

So as to maintain the four semi-rigid elements of the corset in a suitable position, these elements tending to move away from one another under the action of movements of the pelvic muscle, each of the four semi-rigid elements of the corset is connected to each of the two elements adjacent thereto via an elastic junction strip which also occupies the spaces possibly freed by the cutting of the apices of the anterior and posterior elements.

In this case, it is advantageous for the portions of the corset on which there are provided the anterior spring levers, the lateral posterior tighteners and the regulatory elastic means to be located, in the area of the iliac spines, on the elastic junction strips connecting the anterior element and the intermediate elements, as well as on the adjacent edges of these elements.

In the same way, the portions of the corset on which the regulatory elastic means are provided, in the areas of the sacro-iliac joints and ischia, are located on the elastic junction strips between the posterior element and the intermediate elements as well as on the adjacent edges of these elements.

In a simple and practical embodiment, the four semi-rigid elements of the corsets are plates moulded from plastics material provided on an elastic strip, and the regulatory elastic means of the corset are constituted by four elastic strips regulating the the spacing of the intermediate elements of the corset, the two lower strips of which, connecting the portions perpendicular to the iliac spines to the portions perpendicular to the ischia, form brakes limiting the anterior play of the posterior element of the corset and opposing lordosis, whilst the two upper strips connecting the portions perpendicular to the iliac spines to the portions perpendicular to the sacro-iliac joints form brakes opposing kyphosis. In a similar way, the two lateral posterior tighteners are each constituted by an elastic strip. In addition, each of the two lever springs is advantageously constituted by a flexible metal blade able to take account of and restore the flexion and torsion stresses.

In an advantageous manner, on the scapular sub-assembly of each hemithoracic envelope, the pectoral, trapezoidal and sub-spinal elements are equilateral triangles one of whose sides is approximately equal to to the external edge of the shoulder blade and at the level of a semi-rigid sternal element, of substantially rectangular shape, of the common sterno-xyphoidian portion, the trapezoidal element having an apex directed towards the shoulder and its opposite side racing the neck, whilst being connected, along its posterior side, to the upper edge of the sub-spinal element by an elastic junction strip and forming therewith an angle of approximately 15°, the sub-spinal element being connected along its internal side to the dorsal elastic articulation and, along its external side, and by an elastic junction strip, to the posterior thoracic element of the homolateral thoracic sub-assembly, whilst being fixed via its lower apex to the upper end of the homolateral lateral posterior tightener, the trapezoidal element also being connected along its anterior side, and by an elastic junction strip, to the external side of the pectoral element, forming an angle of approximately 15° therewith, and the pectoral element having its upper side facing the clavicle and being inclined by approximately 30° with respect to the sternal element, at the upper end of which the pectoral element is connected by its apex opposite to its external side. In a similar way, on the thoracic sub-assembly of each hemithoracic envelope, which is tensioned between the sub-spinal element of the homolateral scapular sub-assembly and the common sterno-xyphoidian portion, the posterior thoracic, anterior thoracic and xyphoidian elements are equilateral triangles having an apex directed downwardly, the anterior thoracic element being connected, on one hand, along its inner side to the external side of the xyphoidian element by an elastic junction strip and, on the other hand, along its external side to the external side of the posterior thoracic element by an elastic junction strip, forming angles of approximately 60° between these respective sides. It is possible for the sternoxyphoidian portion to be formed from a single element having the sternal element and the two xyphoidian elements. However, each of the two xyphoidian elements is preferably connected by its upper internal apex to the lower end of the sternal element.

In a simple and practical embodiment, the three elements of the scapular sub-assembly and the three elements of the thoracic sub-assembly are, for each hemithoracic envelope, formed by a sequence of six plates in the form of an equilateral triangle moulded from plastics material and provided on an elastic strip. Advantageously, the two anterior lever springs are provided via their upper ends on the corresponding homolateral xyphoidian elements in each case. In addition, the regulatory elastic means connecting the three semi-rigid elements of the scapular sub-assembly on each of the two hemithoracic envelopes are constituted by an elastic tightener anchored at one end to the lower apex of the pectoral element and at the other end to the lower apex of the sub-spinal element, passing through the centre of gravity of the trapezoidal element. In a similar manner, the regulatory elastic means connecting the three semi-rigid elements of the thoracic sub-assembly on each of the two hemithoracic envelopes are constituted by an elastic tightener anchored at one end to the lower apex of the xyphoidian element and at the other end to the lower apex of the posterior thracic element, passing through the centre of gravity of the anterior thoracic element.

In a simple and inexpensive embodiment, the dorsal elastic articulation comprises two elastic members of elliptical shape having a major axis substantially equal to the height of the dorsal column and a minor axis substantially equal to the side of the equilateral triangle elements of the thoracic sub-assemblies, one of the elements having the shape of an elliptical ring with a large central recess, whilst the other element has the shape of an elliptical disc drilled with a small central recess and having an axial slot extending from each of the two ends of its major axis towards its centre, and whose depth is slightly greater than the width of the elliptical ring at the levels of the ends of the major axis of the latter, the disc being engaged in the ring and mounted pivotably with respect to the latter whilst straddling, via its slots, the ends of the major axis of the elliptical ring such that the inner edges of the sub-spinal elements are each held in a gripper constituted by the engagement of half of the elliptical disc and half of the elliptical ring.

Finally, for aesthetic purposes and in order to facilitate the use of the appliance, the lower and upper structures, as well as the spring levers and the tighteners are embedded in the pressure suit.

DESCRIPTION OF THE PREFERRED EMBODIMENT

Figure 1:
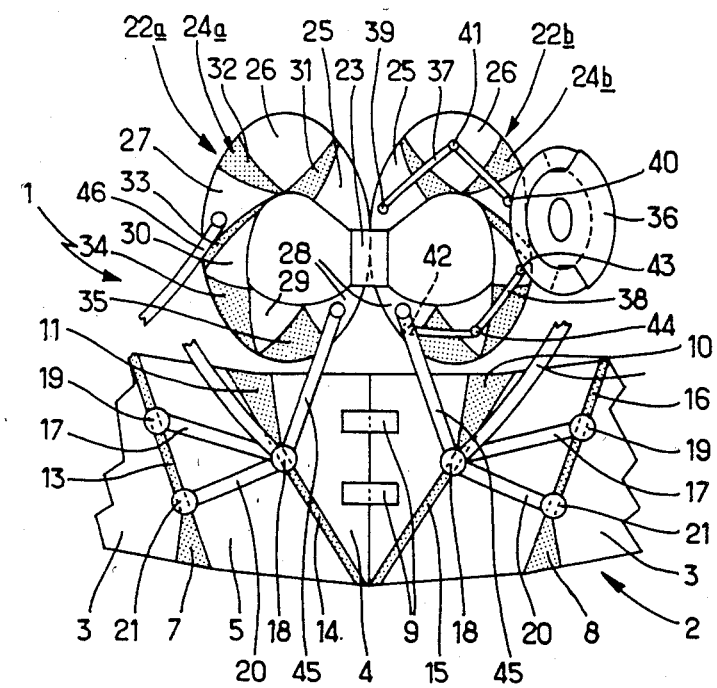
FIG. 1 is a diagrammatic view of the anterior face of an appliance disposed in one plane, with the posterior element of the corset cut away.
Figure 2:
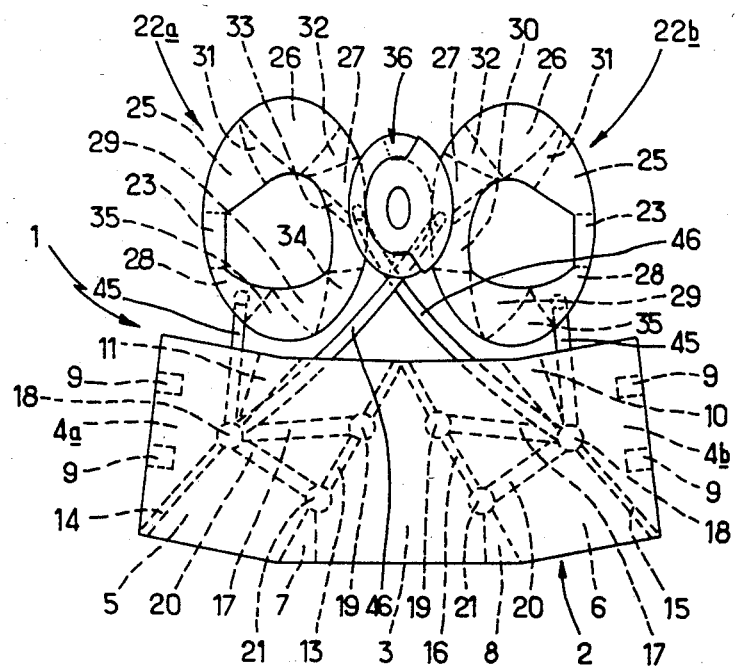
FIG. 2 is a diagrammatic view of the posterior face of the appliance of FIG. 1, disposed in one plane as a result of the opening of the two halves of the anterior element of the corset.
Figure 3:
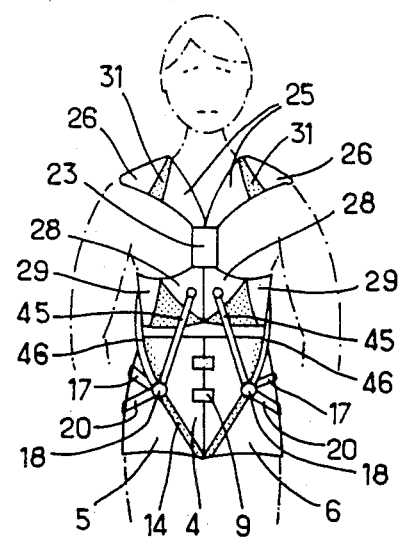
FIGS. 3, 4 and 5 are diagrammatic views from the front, rear and in profile from the right-hand side of a user wearing the appliance.
Figure 4:
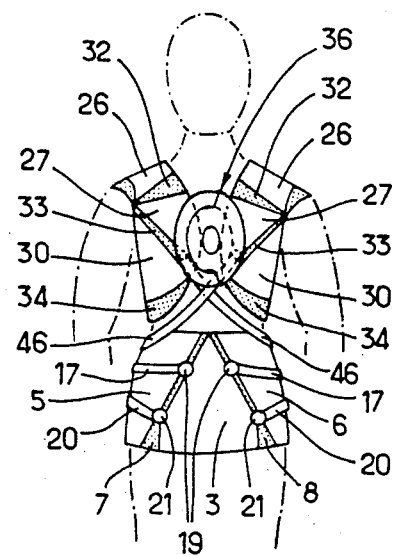
Figure 5:
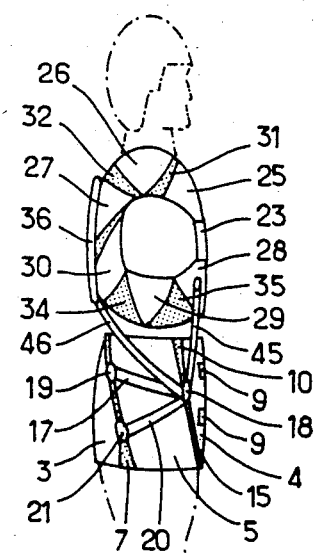

With reference to the drawings, the appliance comprises a pelvic corset 1 essentially comprising an elastic strip 2 on which there are fixed four semi-rigid plates 3,4,5 and 6 having a 2 mm thickness, moulded in plastics material, for example low density polyethylene, and which may be flexibly deformed to a certain extent in all directions.

The elastic strip 2 may have a general rectangular shape but preferably has the shape of a portion of a circular crown having a large radius such that the two small edges of the strip 2 are disposed end to end, the strip 2 has the shape of a frustoconical envelope substantially having the physiological shape of the lower portion of the trunk, i.e. the abdomino-pelvic girdle which the pelvic corset 1 is designed to encircle. The width of the strip 2 is such that it extends from the bi-trochanterian perimeter of the wearer, at the base, to the navel at the top and at the front and to the level of the 3rd or 4th lumbar vertebra at the top at the rear, i.e. the area of the waist. One of the plates 3 fixed in the centre of the strip 2, has the shape of an equilateral triangle whose side is equal to the posterior demi-perimeter of the waist of the wearer. This plate 3, which forms the posterior semi-rigid element of the corset 1, is disposed with one lower horizontal side along the bi-trochanterian posterior demi-perimeter and the opposite upper pointed apex directed vertically upwardly. The two apices adjacent to the lower horizontal side of the plate 3 are cut away by vertical cuts releasing triangular zones 7 and 8 of the elastic strip 2. A further plate 4, forming the anterior semi-rigid element of the corset 1 also has the shape of an equilateral triangle having a size equal to that of the plate 3, although this plate 4 is fixed such that it has an upper horizontal edge on the anterior demi-perimeter of the waist and its opposite lower pointed apex directed vertically downwardly, this plate 4 being divided along a vertical and median line into two halves 4a and 4b each having the shape of a rectangular triangle, and each being fixed on an end portion of the strip 2 such that the two halves 4a and 4b may be joined so as to reconstitute the anterior element 4 when the strip 2 is closed as an envelope around the lower portion of the trunk of the wearer. The halves 4a and 4b support the additional elements of a rapid opening and closing device which enables the two halves 4a and 4b to be joined together so as to close the pelvic corset 1 or to disconnect them from one another so as to open the corset. This device may for example comprise two pairs of complmentary tongues 9 of the closure device sold under the name "Velcro", one tongue of each pair, supporting the hooks, being fixed on the half 4a and the other tongue of each pair supporting the buckles being fixed on the half 4b, the two tongues of the upper paid being substantially at one third of the width of the strip from its upper edge, and the two tongues of the lower pair being substantially at one third of the width of the strip 2 from its lower edge. This appliance has the advantage that it enables immediate regulation to the waist of the wearer of the pelvic corset 1 which opens and closes at the front and may accommodate projections of the abdominal mass.

As in the case of the posterior element 3, the anterior element 4 is cut off at the levels of the two apices adjacent to its upper horizontal edge by two vertical cut-outs (one in each half 4a, 4b) leaving triangular portions 10 and 11 of the strip 2 visible. The cut-outs in the apices of the elements 3 and 4 enable the play of the pelvic motor of the wearer in the case of lordosis or kyphosis. The two other plates 5 and 6 are identical lateral and intermediate elements having the shape of a trapezium or substantially of a parallelogram, disposed symmetrically with respect to the posterior and anterior elements 3 and 4, one of which 5 is interposed between the half 4a and the posterior element 3, whilst the other 6 is interposed between the half 4b and the posterior element 3. The upper substantially horizontal edges of these intermediate elements 5 and 6 are practically identical to the posterior demi-perimeter of the waist. As shown in the drawings, the four elements 3, 4, 5 and 6 are not disposed directly adjacent to one another on the strip 2 but are separated by a play of between 5 and 8 mm releasing strips of elastic junction 12, 13, 14 and 15 which, with the triangular zones 7, 8, 10 and 11 form the only visible portions of the elastic strip 2. These elastic junction strips 13 to 16 hold against the trunk of the wearer the four elements 3 to 6, which respectively cover the sacro-coccygeal region, the public symphysis and the two iliac bones of the wearer and which tend to move away from one another under the action of movement of the pelvic muscles of the wearer. The corset 1 also comprises brakes constituted by four adjustable elastic straps. Two of these straps 17 each connect one of the two portions 18 of the corset 1 perpendicular to the anterior superior iliac spines, i.e. substantially half way up the elastic junctions 14 and 15, and straddling these junctions and the adjacent edges of the rigid elements 4, 5 and 6 to the homolateral portion of the two portions 19 of the corset 1 perpendicular to the sacro-iliac joints, i.e. substantially one third of the way along the elastic junctions 13 to 16 from the upper edge of the corset 1, and straddling these junctions and the adjacent edges of the corresponding elements 3, 5 and 6. The two other straps 20 each connect an attachment point 18 perpendicular to an iliac spine, to the homolateral portion of the two portions 21 of the corset 1 perpendicular to the ischia, i.e. one third of the way along the junctions 13 to 16 from the lower edge, and straddling the adjacent edges of the elements 3, 5 and 6. The two upper straps 17 form brakes opposing the deformation of the pelvic corset 1 in the case of kyphosis, by opposing the anterior play of the posterior element 3, whilst the two lower straps 20 form brakes opposing the deformation of the corset 1 in the case of lordosis, all of the four straps 17 and 20 opposing the spacing of the two lateral intermediate elements 5 and 6.

Above its lower structure, formed by the corset 1, the appliance also comprises an upper structure formed by two thoracic envelopes 22a and 22b, each encircling a hemithorax and symmetrical with respect to a sternal element 23 of rectangular shape, disposed vertically, and also formed by a semi-rigid plate of moulded plastics material. Each of these two envelopes 22a and 22b, having a general frustoconical shape, is constituted by a sequence of six semi-rigid plates, also cast in plastics material, and fixed on an elastic strip 24a, 24b. These six plates, for example of low density polyethylene with a thickness of 2 mm, have the shape of identical equilateral triangles whose side is approximately equal to the external edge of the shoulder blade of the wearer, as well as at the level of the sternal element 23. Each sequence is divided into two sub-assemblies each comprising three plates, these being a scapular sub-assembly or shoulder strap having, from the interior to the exterior, a pectoral element 25, a trapezoidal element 26 and a sub-spinal element 27, and a inferior lateral thoracic sub-assembly having, from the interior to the exterior, a xyphoidian element 28, covering the costal cartilages, an anterior lateral thoracic element 29 covering the sub-mammary region and a posterior lateral thoracic element 30 covering the sub-scapular region (between the 6th and 10th rib), the axillary space and breast regions remaining free.

As in the case of the corset 1, the six semi-rigid elements 25 to 30 of each sequence are not directly adjacent on the corresponding elastic strip, but are separated by pieces of strip forming the elastic junctions of traingular shape. On the shoulder strap, the pectoral element 25 is connected to the upper end of the sternal element 23 by an inferior internal apex and is inclined by approximately 30° with respect to the sternum, having an upper side along the clavicle, and being connected along its external side to the anterior side of the trapezoidal element 26 by an elastic junction 31 opening over an angular segment of approximately 15°. The trapezoidal element 26 has an apex facing the shoulder and its opposite side facing the neck, and is connected along its posterior side to the interior and superior side of the sub-spinal element 27 by an elastic junction 32, opening over an angular segment of approximately 15°. The sub-spinal element 27 has an apex facing the shoulder and defined between its internal and superior side and its external and inferior side, along which it is connected, by an elastic junction 33 in the form of a strip, having a tension adjustment play of approximately 1 cm, to the superior and internal side of the posterior thoracic element of the inferior lateral thoracic sub-assembly. The latter, which is held between the sub-spinal element 27 and the pectoral element 23 is such that its three elements have a side facing the mammary region and its opposite apex downwardly directed. The external side of the posterior lateral thoracic element 30 is connected to the external side of the anterior lateral thoracic element 29 by a triangular elastic junction 34 extending over an angular segment of approximately 60°. In the same way, the anterior lateral thoracic element 29 is connected by its internal edge to the external side of the xyphoidian element 28 by a triangular elastic junction 35 extending substantially over an angular segment of 60°. Finally, the xyphoidian element 28 is fixed to the lower end of the sternal element 23 by its internal superior apex and is joined by its internal edge to the xyphoidian element of the other hemithoracic envelope 22a or 22b.

It should be noted that the two xyphoidian elements 28 which are symmetrical and rigidly fixed to the sternal element 23 could form a single plate with the latter.

Figure 6:
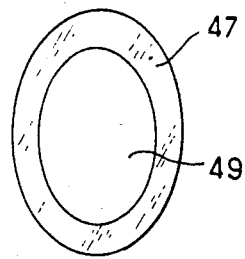
FIGS. 6 and 7 are front views of the two elements of the dorsal elastic articulation of the appliance of FIGS. 1 to 5.
Figure 7:
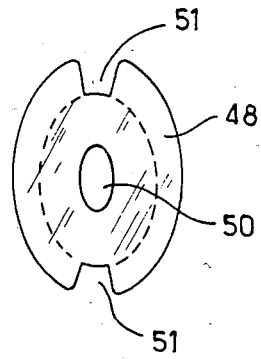
Figure 8:
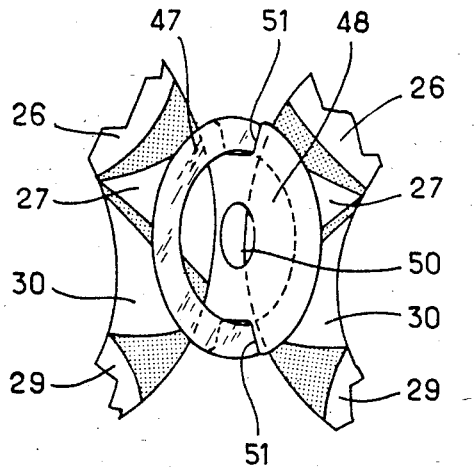
FIG. 8 is a diagrammatic view in perspective showing the engagement of this articulation with the two sub-spinal elements.

In addition, the sub-spinal elements 27 of the two hemithoracic envelopes 22a and 22b are connected together by their internal edge by means of an elastic dorsal articulation 36, described below in detail with reference to FIGS. 6 to 8.

The two frustoconical envelopes 22a and 22b connected together in this way, at the front via the common sternal element 33 and at the rear by the elastic dorsal articulation 36 form to a certain extent diaphragms whose opening and closing are regulated by two brakes 37 and 38 each constituted by an elastic tightener (in order to simplify FIG. 1, the tighteners 37 and 38 are only shown on the hemithoracic envelope 22b, in the upper right-hand portion of FIG. 1). One of the tighteners 37 is fixed on the shoulder strap and is anchored via one of its ends 39 on the internal apex of the pectoral element 25 and via its other end 40 to the internal inferior apex of the sub-spinal element 27, passing into a hoop 41 fixed on the centre of gravity of the trapezoidal element 26. The other tightener 38 is anchored via one of its ends 42 to the inferior apex of the xyphoidian element 28 and via its other end 43 to the inferior apex of the posterior lateral thoracic element 30 passing into a hoop 44 fixed on the centre of gravity of the anterior lateral thoracic element 29.

The lower structure, formed by the pelvic corset 1, and the upper structure, formed by the two hemithoracic envelopes 22a and 22b, are connected together by elastic elements for regulating the dynamic equilibrium of the appliance. These elements comprise, on one hand, two front lever springs 45, each formed by a blade of quenched XC 75 steel having a width of 40 mm and a thickness of 0.5 mm, tensioned between one of the two xyphoidian elements 28, on which it is anchored via its upper end, in the vicinity of the centre of gravity of this element, and the corset 1, on which it is anchored via its lower end to the junction point 18 perpendicular to the homolateral iliac spine. These members also comprise two lateral posterior tighteners 46 each formed by an elastic strap anchored via its upper end to the inferior apex of a sub-spinal element 27 and by its lower end to the junction point 18 located on the corset 1 perpendicular to the controlateral iliac spine.

The elastic dorsal articulation 36, which is centered at the apex of the dorsal column has a general, external, elliptical shape, whose major axis extends vertically over the assembly of the dorsal column, whilst its minor horizontal axis is approximately equal to the side of the identical equilateral triangles formed by the elements 25 to 30. This articulation comprises two elastic members of elliptical shape 47 and 48, one of which is mounted in the other. One of these elements 47 is an elliptical ring having a large central recess 49 of an elliptical shape as well. The other element 48 is an elliptical disc having the same major and minor axes as the ring 47, but having a small central orifice 50, also of elliptical shape, and two axial slots 51, each provided in one end of the major axis towards the centre, and whose depth is slightly greater than the width of the ring 47 in the portions located at the end of its major axis, i.e. such that the ellipse passing through the base of the slots 51 and indicated in dashed lines (corresponding to the elliptical recess 49 of the ring 47) is not discontinuous. In addition, the two slots 51 are slightly widened outwardly so as to facilitate the engagement of the disc 48 in the ring 47 and the introduction of the portions of the ring 47 located at the ends of its major axis into the slots 51 of the disc 48, and so as to facilitate the pivoting of the disc 48 with respect to the ring 47 about their substantially common major axis. This possibility of rotation combined with the elasticity of the two members 47 and 48 enables the formation, when the disc 48 is pivoted with respect to the ring 47 such that its two halves are each substantially applied against a corresponding half of the ring 47, on either side of this latter, of two grippers each of which is formed by the cooperation of the half of the disc 48 and the half of the ring 47 opposite one another, and in which the internal sides of the sub-spinal elements 27 may be retained, as shown in diagram form in FIG. 8.

The posterior junction between the two frustoconical hemithoracic envelopes 22a and 22b is thus ensured by an elastic dorsal articulation 36 having the mechanical advantage that it maintains each of the elements to be joined gripped within two lips each constituted by half of an elliptical elastic element, whose shape matches differential deformations in all diretions of the two hemithoracic envelopes, the central elliptical orifice 50 of the disc 48 also enabling the adjustment of the elastic play of the articulation 36, whose thickness is limited in the area of the junction.

It would of course be possible to use an elastic articulation having a different structure to that described above in order to provide the posterior junction of the hemithoracic envelopes.

The appliance described above therefore comprises three composite, fructoconical envelopes, the lower of which encircles the pelvis in its entirety, and the upper two of which each encircle a hemithorax, these envelopes being provided with elastic means and connected by elastic means, at least one of which is stressed and loaded by any volontary movement of the trunk of the wearer, and then tends as a reaction to bring the trunk into its natural position, in a vertical manner. In effect, the lever springs 45 take account of the movements of flexion of the trunk towards the front and the rear, as well as torsion movements of the trunk on both sides, and are charged in the same way as power stores which tend to discharge when causing the trunk to make the reverse movement. The tighteners 46 operate in a similar way as brakes loaded by a forward movement and opposing any forward fall of the thorax, one of which is loaded during torsion of the trunk and tends to recall in a torsional manner in the opposite direction. In addition, the tightener 37 is loaded during a rearward movement of the corresponding shoulder, and then tends to recall the shoulder and cause it to drop, in particular in response to movements of a screw type, which combine a rotation of the trunk with an elevation of one shoulder and a lowering of the other. Finally, the tightener 38 tends to lock the rib cage and is loaded by a rearward movement. The combined effects of these various elastic means as well as the elastic strips on which the semirigid plates are fixed, in response to any volontary movement of the trunk of the wearer, enable a sufficient reactivation of the scapular and pelvic motor muscles so as to make it possible to use the appliances for the upper and lower limbs described in the two patent applications mentioned above.

The various components of the appliance of the invention, which is preferably embedded in a pressure suit, between two layers of fabric for example, or integrated in support clothing, may be regulated as a function of the static disorders or a lack of anterior posterior and/or lateral and/or torsional balance of the wearer. The appliance enables dynamic balance to be ensured, in the case of high paralysis of the vertebral column, and facilitates the transmission of tensions and movements with respect to the pelvic motor muscles. The appliance of the invention therefore enables positioning disorders to be corrected to a certain extent, enables a certain amplification or replacement with respect to motricity disorders and movement and/or positioning information in the case of sensitivity disorders.

It is obvious that the embodiment described above is in no way limiting and may be modified in any desirable way without departing from the scope of the invention.

What I claim is:

1. An external appliance for the trunk of the body, characterised in that it comprises two composite structures, a first structure being a lower structure having a general frustoconical external shape, for encircling the pelvis and the abdomen of a weareer of the appliance and formed by a pelvic corset extending substantially from the bi-trochanterian perimeter at the bottom up to, on one hand, substantially the navel, at the top at the front and, on the other hand, up to the lower half of the lumbar column, at the top at the rear, the said corset comprising:

a plurality of semi-rigid elements connected by flexible and pliant members and regulatory elastic means connecting each of the two portions of the corset located perpendicular to the two anterior superior iliac spines to the portion of the corset located perpendicular to the homolateral sacro-iliac joint, on one hand, and to the portion of the corset located perpendicular to the homolateral ischium, on the other hand, the second composite structure being an upper structure comprising two symmetrical hemithoracic envelopes each having a general frustoconical external shape and each surrounding a hemithorax, the two hemithoracic envelopes having a common sterno-xyphoidian portion and each having two sub-assemblies, one of which is a scapular sub-assembly and the other an inferior lateral thoracic sub-assembly, each of these two sub-assemblies being constituted by a plurality of semi-rigid elements connected by flexible and pliant members, the regions of the axially space and the breast remaining free, the upper structure also comprising:

a dorsal elastic articulation, centered at the apex of the dorsal column and connecting the two hemithoracic envelopes together in a detachable manner, and regulatory elastic means connecting, on each of the two hemithoracic envelopes, on one hand, the semi-rigid elements of the scapular sub-assembly and, on the other hand, the semi-rigid elements of the thoracic sub-assembly, the two said composite structures being connected together by means for linking and regulating the dynamic equilibrium of the appliance, which comprises:

two front lever springs, tensioned between one of the two portions of the corset located perpendicular to the anterior superior iliac spines and the homolateral portion of the sterno-xyphoidian common portion, the said lever springs being designed to take into account the deformations due to flexion and-/or torsion of the trunk and to regulate the relative movements of the vertebral column, the pelvis and the thoracic assembly, two lateral posterior tighteners connecting in each case the sub-spinal zone of the scapular sub-assembly of one of the hemithoracic envelopes to the portion of the corset located perpendicular to the iliac spine of the opposite side, the said tigheners being designed to prevent the thorax from falling forwards.

2. An appliance as claimed in claim 1, characterised in that the corset comprises four semi-rigid elements, the two first elements being substantially identical and having approximately the form of an equilateral triangle whose side is substantially equal to the demi-perimeter of the waist, one of the said first elements being a posterior element which is disposed on the sacro-coccygeal region such that its lower side is disposed along the bi-trochanterian posterior demi-perimter and the other of the said first elements is a front element which is disposed on the public symphsis such that its upper side is disposed along the anterior demi-perimeter of the waist, the two other semi-rigid elements of the corset being substantially identical and having a trapezoidal shape, each located in an intermediate position between the first anterior and posterior elements, the upper side of these trapezoidal elements being disposed at the level of the waist and being substantially equal to the demi-perimeter of the waist, these two intermediate elements being disposed symmetrically on each side on the two iliac bones.

3. An appliance as claimed in claim 2, characterised in that the anterior semi-rigid element of the corset is sub-divided along the vertical median line into two halves supporting the additional means of an opening and closing mechanism of the two halves, so as to enable the corset to be opened and closed at the front.

4. An appliance as claimed in claim 3, characterised in that the two apices adjacent to the horizontal side of the anterior and posterior triangular elements of the corset are cut away, so as to define free spaces enabling movements of the pelvis.

5. An appliance as claimed in claim 4, characterised in that each of the four elements of the corset is connected to each of the two elements adjacent theretoby an elastic junction strip which also occupies the spaces possibly released by the cutting away of the apices of the posterior and anterior elements.

6. An appliance as claimed in claim 5, characterised in that the positions of the corset on which there are fixed the front lever springs, the lateral posterior tighteners and the regulatory elastic means in the area of the iliac spines, are located on the elastic junction strips connecting the anterior element to the intermediate elements as well as on the adjacent edges of these elements.

7. An appliance as claimed in claim 6, characterised in that the portions of the corset on which there are fixed the regulatory elastic means in the areas of the sacro-iliac joints and the ischia, are located on the elastic junction strips between the rear element and the intermediate elements as well as on the adjacent edges of the elements.

8. An appliance as claimed in claim 7, characterised in that the four semi-rigid elements of the corset are plates moulded from plastics material and fixed on an elastic strip.

9. An appliance as claimed in claim 2, characterised in that the regultory elastic means of the corset ae constituted by four elastic strips regulating the spacing of the intermediate elements of the corset, the two lower strips of which connecting the portions perpendicular to the iliac spines to the portions perpendicular to the ischia, form brakes limiting the forward play of the posterior element of the corset and opposing lordosis, whilst the two upper strips connecting the portions perpendicular to the iliac spines to the portions perpendicular to the sacro-iliac joints form brakes opposing kyphosis.

10. An appliance as claimed in claim 1, characterised in that the two lateral posterior tighteners are each formed by an elastic strip.

11. An appliance as claimed in claim 1, characterised in that each of the two lever springs is constituted by a flexible metal blade able to take account of and restore flexion and torsion stresses.

12. An appliance as claimed in claim 1 characterised in that each of the two sub-assemblies of the second composite structure is constituted by three semi-rigid elements connected by flexible and pliant memers, these three semi-rigid elements being, for the scapular sub-assembly, a pectoral element, a trapezoidal element and a sub-spinal element and, for the thoracic sub-assembly, a posterior thoracic element located on the sub-scapular region, an anterior thoracic element located on the sub-mammary region, and a xyphoidian element located on the costal cartilages and belonging to the common streno-xyphoiidian portion, the two hemithoracic envelopes being connected by the elastic dorsal articulation at the level of the sub-spinal elements of their sub-scapular assemblies.

13. An appliance as claimed in claim 12, characterised in that, in the case of the scapular assembly of each hemithoracic envelope, the pectoral trapezoidal and sub-spinal elements are equilateral triangles whose side is approximately equal to the external edge of the shoulder blade and at the level of a semi-rigid sternal element of substantially rectangular shape, of the common sterno-xyphoidan portion, the trapezoidal element having an apex directed towards the shoulder and its opposite side facing the neck, whilst being connected by its rear edge to the upper side of the sub-spinal element by an elastic junction strip and forming therewith an angle of approximately 15°, the sub-spinal element being connected by its inner edge to the dorsal elastic articulation and by its external edge to an elastic junction strip attaching it to the posterior thoracic element of the homolateral thoracic sub-assembly, whilst being fixed by its lower apex to the upper end of the homolateral posterior tightener, the trapezoidal element also being connected along its front edge, and via an elastic junction strip to the external edge of the pectoral element, forming therewith an angle of approximately 15° and the pectoral element having its upper side facing the clavicle and being inclined by approximately 30° with respect to the sternal element, at the upper end of which the pectoral element is connected by its apex opposite to its external edge.

14. An appliance as claimed in claim 13, characterised in that, in the case of the thoracic sub-assembly of each hemithoracic envelope, which is tensioned between the sub-spinal element of the homolateral scapular sub-assembly and the common sternoyphoidian element, the posterior thoracic, anterior thoracic and xyphodian elements are equilateral triangles having a downwardly directed apex, the anterior thoracic element being connected on one hand along its inner edge to the external edge of the xyphoidian element by an elastic junction strip and, on the other hand, along its external edge to the external edge of the posterior thoracic element by an elastic junction strip forming angles of approximately 60° between these respective sides.

15. An appliance as claimed in claim 14, characterised in that the common sterno-xyphoidian element is formed from a single component having the sternal element and the two xyphiodian elements.

16. An appliance as claimed in claim 15, characterised in that each of the two triangular xyphoidian elements is connected by its superior internal apex to the lower end of the sternal element.

17. An appliance as claimed in claim 16, characterised in that, for each hemithoracic envelope, the three elements of the scapular sub-assembly are formed by a sequence of six plates formed as equilateral triangles moulded in plastics material and fixed on an elastic strip.

18. An appliance as claimed in claim 17, characterised in that the two anterior lever springs are fixed by their upper end onto the corresponding homolateral xyphoidian element in each case.

19. An appliance as claimed in claim 18, characterised in that the regulatory elastic means connecting the three semi-rigid elements of the scapular sub-assembly to each of the two hemithoracic envelopes are formed by an elastic tightener anchored at one end to the lower apex of the pectoral element and at the other end to the lower apex of the sub-spinal element, passing through the centre of gravity of the trapezoidal element.

20. An appliance as claimed in claim 19, characterised in that the regulatory elastic means connecting the three semi-rigid elements of the thoracic sub-assembly to each of the two heithoracic envelopes are formed by an elastic tightener anchored at one end to the lower apex of the xyphoidian element and at the other end to the lower apex of the posterior thoracic element and pass through the centre of gravity of the anterior thoracic element.

21. An appliance as claimed in claim 12, characterised in that the dorsal elastic articulation comprises two elastic members of elliptical shape having a major axis substantially equal to the height of the dorsal column and a minor axis substantially equal to the side of the elements shaped as equilateral triangles of the thoracic sub-assemblies, one of these members having the shape of an elliptical ring with a large central recess, whilst the other is shaped as an elliptical disc drilled with a small central recess and has an axial slot extending from each edge of its major axis towards is centre, the depth of the said axial slot being slightly greater than the width of the ring at the levels of the ends of its major axis, the disc being engaged in the ring and pivotably mounted with respect to the latter, straddling via its slots the ends of the major axis of the ring such that the inner edges of the sub-spinal elements are each held in a gripper constituted by the engagement of a half of a disc and a half of the ring.

22. An appliance as claimed in claim 1 characterised in that the lower and upper structures, the spring levers and the tighteners are embedded in a pressure suit.

* * * * *